(12) United States Patent
Dobler et al.

(10) Patent No.: US 11,013,821 B2
(45) Date of Patent: May 25, 2021

(54) FOLDED OR MULTI-LAYERED PAPER AIR FRESHENER

(71) Applicants: Sven Dobler, Huntington, NY (US); Russell Ostroff, West Islip, NY (US); Valeriano Marinelli, Port Washington, NY (US)

(72) Inventors: Sven Dobler, Huntington, NY (US); Russell Ostroff, West Islip, NY (US); Valeriano Marinelli, Port Washington, NY (US)

(73) Assignee: Orlandi, Inc, Farmingdale, NY (US)

( * ) Notice: Subject to any disclaimer, the term of this patent is extended or adjusted under 35 U.S.C. 154(b) by 190 days.

(21) Appl. No.: 16/350,216

(22) Filed: Oct. 15, 2018

(65) Prior Publication Data
US 2019/0117819 A1    Apr. 25, 2019

Related U.S. Application Data

(60) Provisional application No. 62/707,188, filed on Oct. 24, 2017.

(51) Int. Cl.
| | |
|---|---|
| *A61L 9/04* | (2006.01) |
| *D21H 21/14* | (2006.01) |
| *B32B 27/12* | (2006.01) |
| *B32B 5/02* | (2006.01) |
| *B32B 27/10* | (2006.01) |
| *B32B 7/12* | (2006.01) |
| *D21H 27/30* | (2006.01) |

(Continued)

(52) U.S. Cl.
CPC ............. *A61L 9/042* (2013.01); *A61L 9/04* (2013.01); *B32B 5/022* (2013.01); *B32B 7/12* (2013.01); *B32B 27/10* (2013.01); *B32B 27/12* (2013.01); *D21H 19/22* (2013.01); *D21H 21/14* (2013.01); *D21H 27/10* (2013.01); *D21H 27/30* (2013.01); *A61L 2209/13* (2013.01); *A61L 2209/15* (2013.01)

(58) Field of Classification Search
CPC . A61L 9/042; A61L 9/04; A61L 9/044; A61L 9/046; A61L 2209/13; A61L 2209/131; A61L 2209/15; B32B 5/022; B32B 7/12; B32B 27/10; B32B 27/12; D21H 9/22; D21H 21/14; D21H 27/10; D21H 27/30
USPC .................................... 239/34, 57; 428/905
See application file for complete search history.

(56) References Cited

U.S. PATENT DOCUMENTS

| | | |
|---|---|---|
| 4,163,518 A | 8/1979 | Webinger |
| 4,166,565 A | 9/1979 | Webinger |

(Continued)

*Primary Examiner* — Steven J Ganey
(74) *Attorney, Agent, or Firm* — Paul M Denk

(57) ABSTRACT

A paper air freshener, that may be folded into a multi-layered freshener, and may have other layers of polymer, or the like, applied thereto, with the concept of layering said freshener after being saturated or having absorbed the fragrance material, at the various layer levels, provides for a more gradual and controlled release of the fragrance to the ambient air during usage. The layers of paper may be laminated, or may be folded integrally from a singular paper structure, and secured together by various connectors, in preparation for its usage and application. The other layer of polymer forming a seal layer, and being debossed to form a well, into which fragrance material may be applied, during the assembly of the paper air freshener.

11 Claims, 5 Drawing Sheets

(51) Int. Cl.
*D21H 27/10* (2006.01)
*D21H 19/22* (2006.01)

(56) References Cited

U.S. PATENT DOCUMENTS

| | | | |
|---|---|---|---|
| 4,270,692 A | | 6/1981 | Webinger |
| 4,279,373 A | | 7/1981 | Montealegre |
| 4,280,649 A | | 7/1981 | Montealegre |
| 4,280,651 A | | 7/1981 | Montealegre et al. |
| 5,383,598 A | | 1/1995 | Styles |
| 5,395,047 A | * | 3/1995 | Pendergrass, Jr. ........ A61L 9/12 239/34 |
| 5,529,243 A | | 6/1996 | Hoyt et al. |
| 5,788,155 A | | 8/1998 | Martin et al. |
| 6,328,952 B1 | | 12/2001 | Alboum et al. |
| 7,523,577 B2 | | 4/2009 | Majerowski et al. |
| 7,665,238 B2 | | 2/2010 | Majerowski |
| 7,926,734 B2 | | 4/2011 | Dobler et al. |
| 7,926,735 B1 | | 4/2011 | Mobley |
| 8,777,127 B2 | | 7/2014 | Bernstein |
| 8,968,647 B2 | | 3/2015 | Fscher et al. |
| 9,248,210 B2 | | 2/2016 | Kunesh |
| 9,486,551 B2 | | 11/2016 | Granger et al. |
| 9,642,928 B1 | | 5/2017 | Rapoza |
| RE46,612 E | | 11/2017 | Bernstein |
| 2004/0256480 A1 | * | 12/2004 | Channer ................ A61L 9/048 239/34 |
| 2007/0014993 A1 | * | 1/2007 | Longmoore ............ B32B 27/18 428/500 |

\* cited by examiner

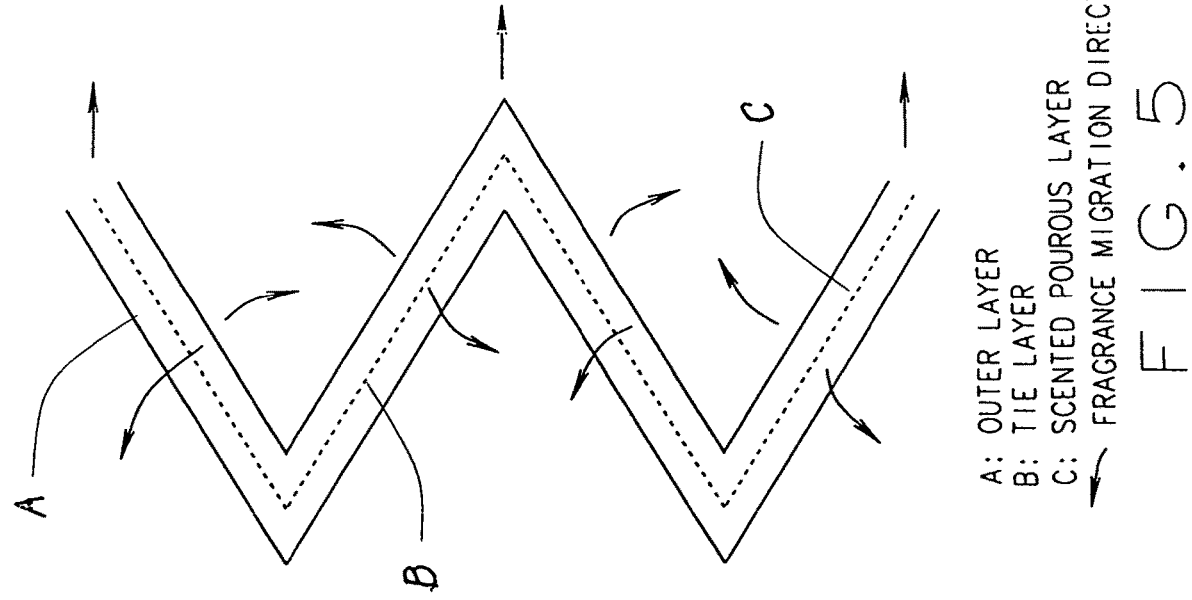
FIG. 3
PRINTED PAPER
TIE LAYER
SYNTHETIC/NON-WOVEN
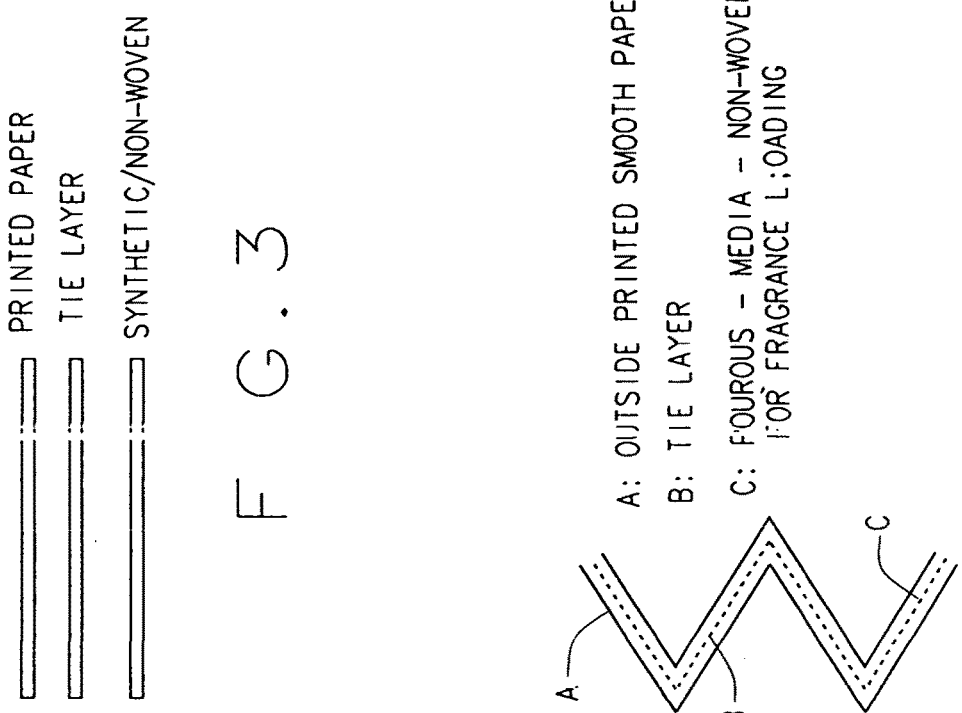
FIG. 4
A: OUTSIDE PRINTED SMOOTH PAPER
B: TIE LAYER
C: POUROUS - MEDIA - NON-WOVEN FOR FRAGRANCE L;OADING
FIG. 5
A: OUTER LAYER
B: TIE LAYER
C: SCENTED POUROUS LAYER
FRAGRANCE MIGRATION DIRECTION A: SUBSTRATE PIECE TOP    B: SUBSTRATE PIECT BOTTOM
S: SEAL OR ATTACHMENT     D: DEBOSSED WELL
FM: FRAGRANCE MATERIAL
A AND B ARE SEPARATE AND NOT CONNECTED BY FOLD A: SUBSTRATE TOP/BOTTOM CONTINOUS    F: FOLD
$S_1$: PERIMETER SEAL    $S_2$: OPTIONAL SEAL    FM: FRAGEANCE MATERIAL

FOLDED OR MULTI-LAYERED PAPER AIR FRESHENER

CROSS REFERENCE TO RELATED APPLICATION

This application is a non-provisional patent application to the provisional filed under Ser. No. 62/707,188, which was filed on Oct. 24, 2017.

FIELD OF THE DISCLOSURE

Paper air fresheners are made of paper of various thicknesses, and are decorated by printing by various methods, and then have a string or hook for suspension, and are packaged, into their final form for marketing. This invention generally includes a series of paper laminates, or paper stock, saturated with a fragrance, which when the folds or layers are opened, a fresh layer of fragrance is released, for prolonged application of the air freshener.

BACKGROUND OF THE INVENTION

Paper air fresheners have been in use for many decades. Generally, you can see them suspended from the rear view mirror of an automobile, or applied at other vicinities, for use for refreshing the ambient air of the proximate space. There are many patents upon this type of concept, in the prior art.

Many of these prior art paper fresheners are made of paper, of various thicknesses, and are decorated by printing either by lithographic, offset, flexography, or silkscreen. They are scented with fragrance materials, they are cut, strung, and are packaged into their final form.

Usually, paper air fresheners are less expensive to make than other air freshening devices, and their effectiveness in scenting a small space is tied to various factors including the amount, composition, and endurance of the fragrance materials utilized. Also, the thickness, porosity, chemical nature, absorption characteristics of the paper carrier used, and finally, the surface area, as the surface areas where the fragrance materials are released to the air, are the characteristics of paper air fresheners.

Most paper air fresheners release their fragrance in the first few days at a high rate, and then loose power and effectiveness as the fragrance materials evaporate into the ambient air.

Papers that release slowly also tend to be more dense, and absorb more slowly, and take less of a fragrance load overall. They often print better, however, as they have smoother surfaces, they are generally less effective as small space air fresheners.

Papers that release more readily are more absorbent and can take more of the fragrance load overall. But, they often print worse as the surface is more open and rough, of texture. They are generally more effective as a small space air freshener.

SUMMARY OF THE INVENTION

This invention contemplates a folded paper air freshener, that would be more effective, and longer lasting, when prepared for application, and utilized for adding fragrance to a surrounding vicinity, whether it be within a room, a vehicle, or any other related space.

There is a balance to be found and compromise to be made, therefore, where aspects of printability, fragrance load, and release profiles intersect and constrain each other, and this is what is being addressed by this current invention.

This invention uses the features and characteristics of various different substrates, and combines them into a multi-layer carrier ("MLC"). Generally, it includes one or more plys of paper that are laminated or tacked or secured together to form the paper air freshener of this invention.

The invention further provides an additional layering as this new MLC material is folded on itself either once, twice, three or more times, thus creating barriers to the outside surface upon which fragrance releases to the air.

The invention further provides a very absorptive substrate layer, that can receive a high fragrance load.

The invention further provides a smooth printable graphic layer, which is important for the commercial aspects of the application of the invention in a marketing sense.

The invention further provides a tie layer that acts as a membrane or barrier to reduce the rate of migration of the fragrance materials from the absorptive layer, to the outside graphic layer, where it evaporates into the atmosphere.

These and other objects of this may become more apparent to those skilled in the art upon review of the summary of the invention as provided herein, and upon undertaking a study of the description of its preferred embodiment, in view of the drawings.

BRIEF DESCRIPTION OF THE DRAWINGS

FIG. 3 provides a side view of the substrate, and the various layers that make up the paper or other synthetic layers of the air freshener;

FIG. 4 discloses a folded air freshener, in this instance, comprising a four panel air freshener, after it is folded into its usable configuration;

FIG. 5 shows the fragrance migration directions, through the folded layers, as the fragrance is disseminated into the ambient air;

DESCRIPTION OF PREFERRED EMBODIMENT

Figure 1:
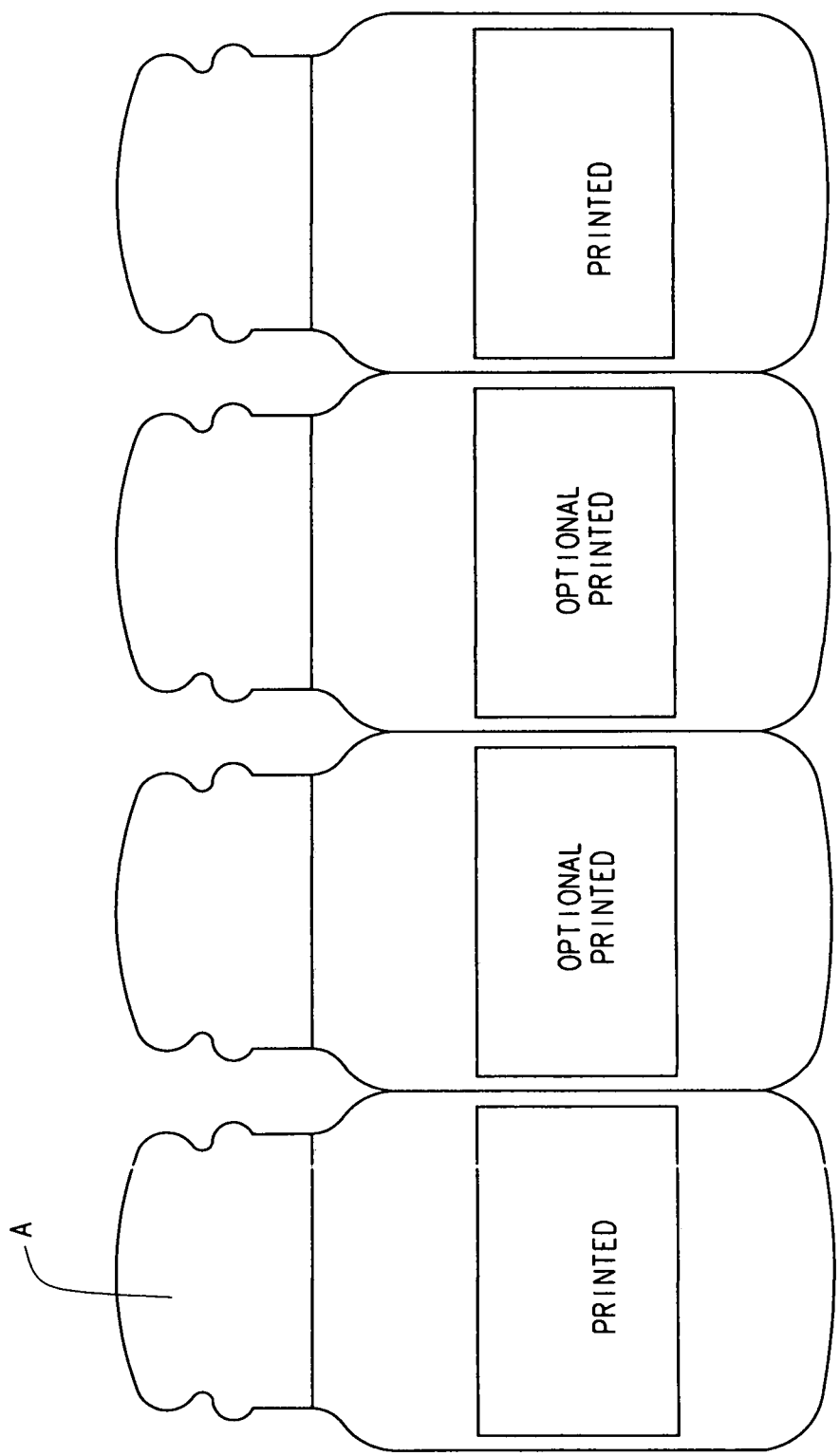
FIG. 1 shows the air freshener front, that includes a printed layer, an optional printed layer, a further optional printed layer, and the printed layer as noted. Thus, this would be a four layer paper air freshener.

As can be noted in the drawings, and in particular FIG. 1, the top material "a" of FIG. 1, and FIG. 4, are smoothly calendared, printable paper, such as sixty pound, more or less, text stock. The paper may be clay coated, or uncoated, but the uncoated is the preferred embodiment, since it may absorb the fragrance material more readily.

The tie-layer, as noted at "b" in FIG. 4, can be any adhesively mounted permeable polymer film. Polyethylene is the preferred embodiment. Alternatively, PE or other polymers can also be extruded to create a tie-layer between the layers "a" and "c".

The bottom material, as at "c" in FIG. 4, should be an absorbent material. This can be a synthetic non-woven, flocking, design for optimal fragrance loading, and inert and is resistant to fragrance materials.

Figure 2:
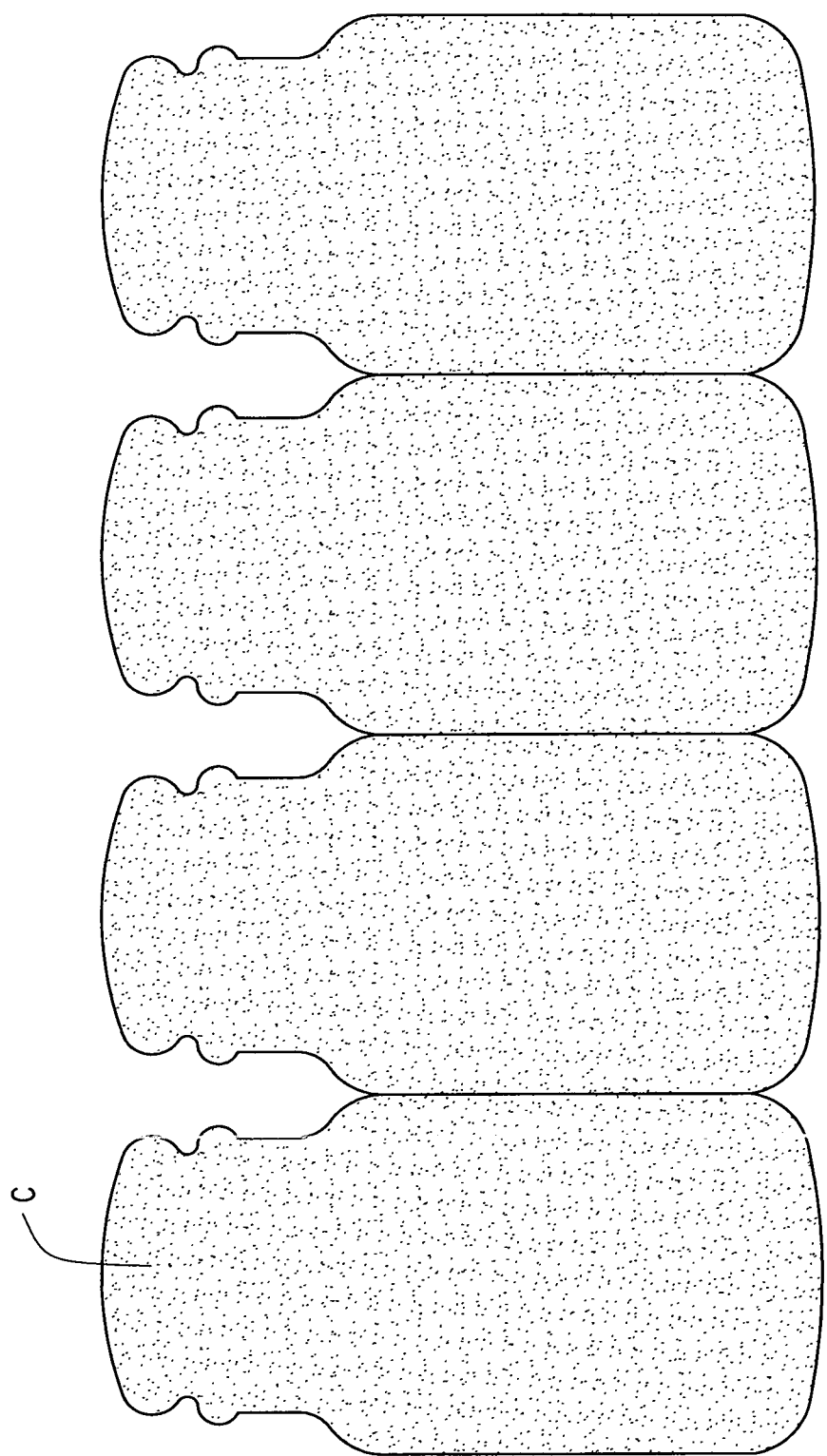
FIG. 2 discloses the back of the air freshener, which is not decorated or printed, as can be noted.

Once the multi-layer substrate, "MLC" is printed, scented, converted to size, it can be folded upon itself to create a multi-layer air freshener. FIG. 1, FIG. 2, and FIG. 5, show the example of a four-panel folded air freshener. FIG. 5 also shows how the fragrance is embedded in layer "c" and must pass through the permeable tie-layer barrier "b" before it can evaporate off of the large paper substrate area "a". The choice of the tie-layer will determine the rate of migration, as any permeable tie-layer will allow permeation to various degrees and rates of migration. The choice of absorbent layer "c" will determine the amount of fragrance load that is possible for usage. The thicker the layer, the more fragrance that can be loaded therein, as can be understood.

Figure 6:
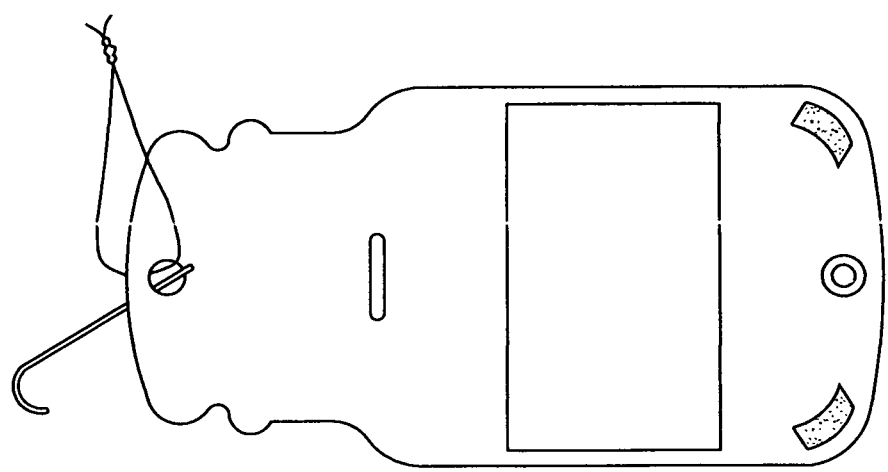
FIG. 6 discloses the folded attachment and the various options or other components that may be added to the air freshener, such as an upper aperture for holding a cord or for T-hook, a lateral slot for holding the layers together, and a bottom grommet, and the sonic or adhesive seals that hold the layers together.

The folded air freshener can be held together in various fashions, by way of example, as shown in FIG. 6. The folded paper or other material freshener can have a shrink band applied around its body, after folding, for the formed air fresher. A hole as punched and stringing can be applied to the top, as noted. A hole punching and placing of a hook or clip, may be applied to the top of the freshener, for use for suspension. Also, a sonic high frequency sealing and securing of the layers together, can be applied. A mechanical attaching of the folded layers together, with staples, grommets, clips, and other attachment devices, can be utilized. In addition, an adhesive sealing may be applied, or spot applied, where noted. Finally, creating a tab on panel 1, or the back panel, and various slots applied upon the panels 2, 3, or 4, can allow the various panels to be locked together, by inserting the tab through the various aligned slots.

Various common secondary packaging options may also include flow wrapping, header card attachments, for peg board at retail, cartons, and other type displays, to which the fresheners may be applied.

Additional options include the perforating of the folds of the MLS so that the MLS levels can be separated and removed by users, overtime, to access inner layers that may carry more fragrance materials, for further dissemination, as can be noted in FIG. 6. Furthermore, using micro-encapsulated fragrances on absorbent substrate layers, as "c", so that upon separating of the MLS folded layers, the fragrance is released in time through the micro-encapsulated breakage, when the folded adjacent layers are unfolded, as can be understood. Furthermore, creating a two-panel, four, six, eight-panel, or multipanel versions of this invention, are readily comprehended for application of the subject matter of this invention.

Figure 7:
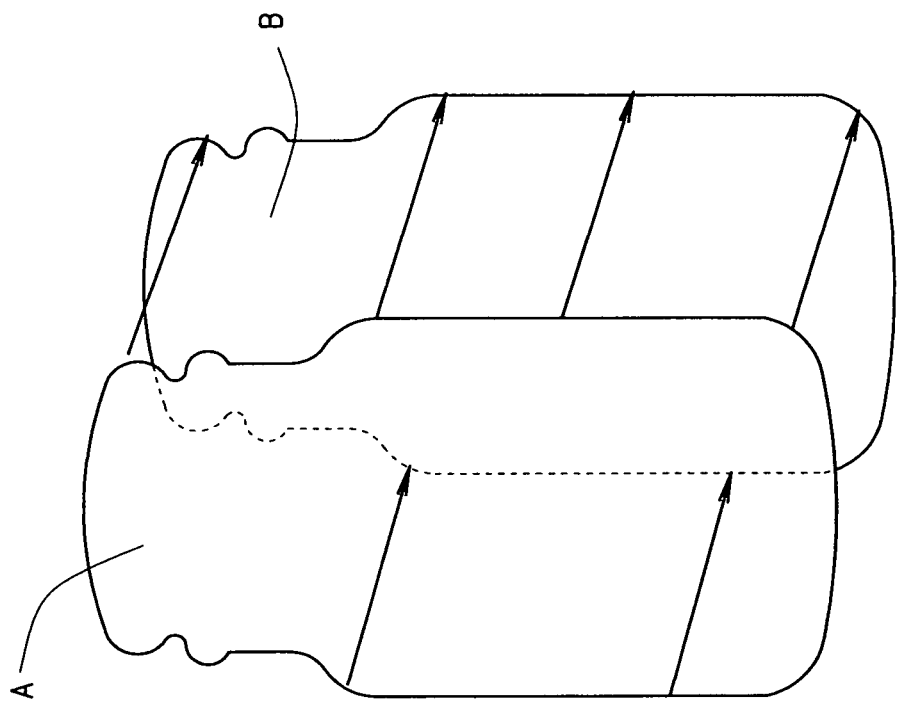
FIG. 7 shows a pair of paper panels "a" and "b", which may be partially laminated together, after being saturated with a fragrance, to function as a multi-layered paper air freshener for this invention.
Figure 7A:
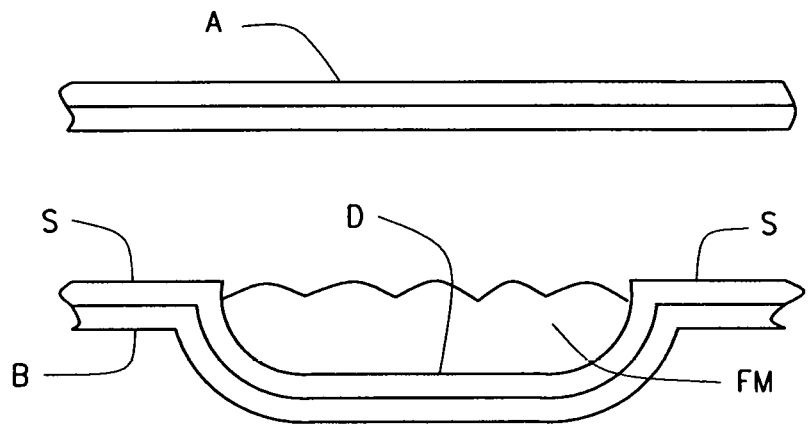
FIG. 7a shows how the substrate "a" and the substrate "b" appear in cross-section, and a seal layer forming a well is disposed intermediate the layers "a" and "b".

FIG. 7 shows a pair of layers "a" and "b", made of paper, and which may be saturated with a fragrance upon their interior surfaces. The external surfaces of the layers "a" and "b" may be capable of accepting print material, for display or advertising purposes. These layers "a" and "b" may be laminated together, and held in position by means of a seal layer, as noted at "s" in FIG. 7a. In addition, the seal layer and the bottom layer "b" may be embossed to form a well d, and into which fragrant material "fm" may locate to have further supply of the fragrance material to the freshener, in preparation for its usage. And, while the embodiment of FIGS. 7 and 7a show how the paper sampler may be laminated together, and may be sealed around their periphery, or sealed at other locations, such as the spot seals as previously reviewed, in their laminated form the paper air freshener may be suspended for usage and application. When it is desired to enhance the flow of fragrance material and its aroma from the sampler, the laminates may be partially or fully separated, to allow for the outflow of the fragrance material from it.

Figure 7B:
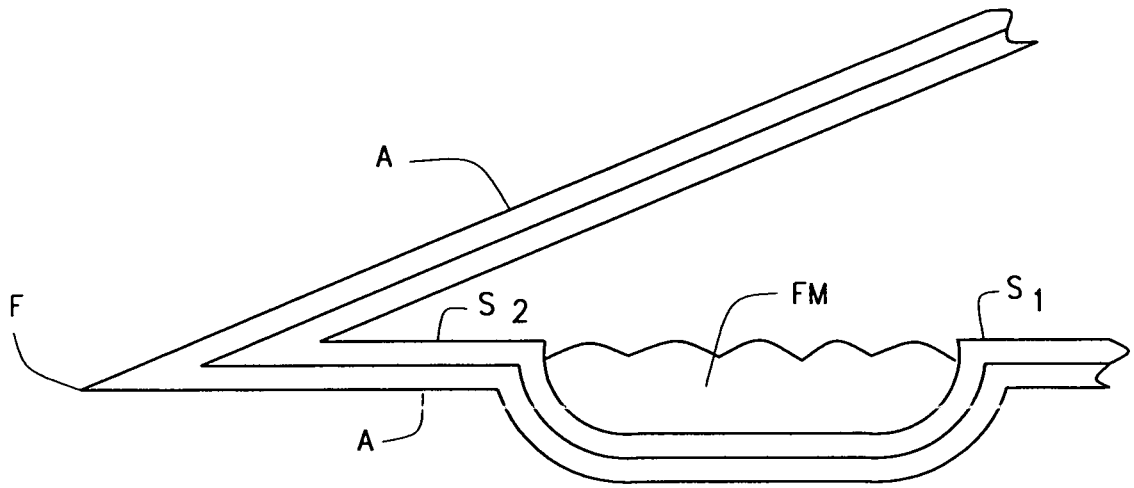
FIG. 7b shows how the substrate "a" may be folded, along one edge, forming a well within its seal intermediate layer.

Or, as can be noted in FIG. 7b, one of the laminated layers, such as the layer "a", may be folded over, forming its fragrance material holding debossed well, as previously noted at d, and the seal layer, which may be formed of polyethylene, or any other related firm material, that is impervious to liquid migration, may be formed therein, and have seals supplied at "s2", as noted, so as to seal in its fragrance material within the folded fly "a", as can be noted. And, when partial or full separation occurs, the fragrant material may disseminate its aroma into the ambient air, to provide for effective usage of the sampler, during application. Obviously, the seals "s2" can be placed at any location along the film material, to provide for even partial migration of fragrance from the paper air freshener, during its usage and application.

Other variations upon this invention may be entertained by those skilled in the art, upon reviewing the summary of this invention, and upon undertaking a study of the description of its preferred embodiments, in view of the drawings. These disclosures, and the depiction of the invention in the drawings, are primarily set forth for illustrative purposes only. Such variations, if within the spirit of this invention, are intended to be encompassed within the scope of any claims to patent protection issuing herein.

We claim:

1. A paper air freshener made up of layers of paper, which can be folded from a single paper panel, includes the absorption of fragrance material at all levels of the paper air freshener, securing means holding the various layers of the paper together, and when applied for usage, various of the layers of the paper may be separated, to disseminate a fresh layer of fragrance material to the surrounding atmosphere, when used wherein the paper air freshener formed from said folded single paper panel includes an intermediate layer of a tie-layer seal formed of polymer film and which contains the fragrance material to prevent its dissemination into the air until the tie-layer seal it partially or fully separated.

2. The invention of claim 1, and including a bottom layer of synthetic non-woven material applied to the back of the paper air freshener in preparation for its usage, and to prevent any evaporation of the fragranced material from the back side of the said air freshener.

3. The invention of claim 2, including said paper air freshener having front and back layers, a tie-layer applied intermediate the various layers of the folded paper air freshener, to provide a tie-layer between the front and back layers of the formed freshener, and said tie-layer being a polymer film permeable to allow for passage of any fragrance therethrough.

4. The invention of claim 3, wherein the polymer film comprises polyethylene.

5. The invention of claim 1, wherein the tie-layer seal film being formed as a debossed well, to provide a well into which the fragrant material may be deposited during assembly, and said tie-layer seal then being connected between the folded single paper-panel, to seal in the applied fragrant material until such time as full or partial separation of the seal layer is affected.

6. The invention of claim 1, wherein the layers of paper forming the paper air freshener comprises said folded single paper panel folded into four panels for forming the paper air freshener.

7. The invention of claim 1 wherein the fragrance material is formed as micro-encapsulated fragrance material.

8. A paper air freshener made up of laminated layers of paper, which can be layered together, includes the absorption of fragrance material at all levels of the paper air freshener, securing means holding the various layers of the paper together, and when applied for usage, various of the layers may be separated, to disseminate a fresh layer of fragrance material to the surrounding atmosphere, when used, wherein the paper air freshener is made up of said laminated layers of paper, and having a seal layer applied therein, and which once partially or fully sealed with the laminated layers, prevents the dissemination of the aroma of the fragrance material to the surrounding atmosphere until such time as the laminated layers are fully or partially separated in preparation for release of a fragrance during usage, wherein the seal layer is debossed to form a well, and into which the fragrance material locates, with said seal layer and laminated layers of paper being sealed together, until such time as the seal layer is partially or fully separated from the laminated layers to allow for dissemination of fragrance material to the surrounding atmosphere when used.

9. The invention of claim 8, wherein the laminated layers forming the paper air freshener are formed of four layers of paper laminated together.

10. The invention of claim 8 wherein the bottom of the laminated layer is formed of an absorbent material which may be made of synthetic non-woven or flocking material.

11. The invention of claim 8 wherein the laminated layers of paper are formed of approximately 60 lb. text stock.

* * * * *